United States Patent
Wolfe et al.

(10) Patent No.: US 8,741,491 B2
(45) Date of Patent: Jun. 3, 2014

(54) IONIC LIQUID CONTAINING SULFONATE IONS

(75) Inventors: Derek Wolfe, Scottsdale, AZ (US); Cody A. Friesen, Fort McDowell, AZ (US); Paul Bryan Johnson, Phoenix, AZ (US)

(73) Assignee: Fluidic, Inc., Scottsdale, AZ (US)

( * ) Notice: Subject to any disclaimer, the term of this patent is extended or adjusted under 35 U.S.C. 154(b) by 22 days.

(21) Appl. No.: 13/448,923

(22) Filed: Apr. 17, 2012

(65) Prior Publication Data

US 2012/0321967 A1 Dec. 20, 2012

Related U.S. Application Data

(60) Provisional application No. 61/498,308, filed on Jun. 17, 2011.

(51) Int. Cl.
| | |
|---|---|
| *H01M 8/22* | (2006.01) |
| *C07D 471/04* | (2006.01) |
| *C07D 487/08* | (2006.01) |
| *C07D 233/58* | (2006.01) |
| *C07C 309/08* | (2006.01) |
| *C07C 309/14* | (2006.01) |

(52) U.S. Cl.
USPC ........ 429/403; 544/116; 544/349; 548/335.1; 546/121; 562/107; 562/112

(58) Field of Classification Search
USPC ............... 429/403; 544/116, 349; 514/485, 514/252.16; 546/105, 250, 121; 502/167; 548/335.1; 562/112, 107
See application file for complete search history.

(56) References Cited

U.S. PATENT DOCUMENTS

| | | | |
|---|---|---|---|
| 3,519,631 A * | 7/1970 | Ost et al. ................. | 546/105 |
| 4,034,107 A * | 7/1977 | King et al. ............... | 514/485 |
| 5,061,603 A * | 10/1991 | Hamilton et al. .......... | 430/287.1 |
| 2002/0132973 A1* | 9/2002 | Condon et al. ............ | 530/317 |
| 2005/0171355 A1* | 8/2005 | Kuwabara et al. ......... | 546/250 |
| 2006/0069169 A1* | 3/2006 | Li et al. ................... | 518/726 |
| 2006/0217584 A1 | 9/2006 | Nunez et al. | |
| 2008/0021037 A1* | 1/2008 | Beylin et al. ............. | 514/252.16 |
| 2008/0251759 A1 | 10/2008 | Kalb et al. | |
| 2009/0029948 A1* | 1/2009 | Filippini et al. .......... | 514/114 |
| 2009/0270248 A1* | 10/2009 | Earl et al. ................. | 502/167 |
| 2010/0016603 A1* | 1/2010 | Sonoda et al. ............ | 546/250 |
| 2010/0137460 A1 | 6/2010 | Bert et al. | |
| 2010/0285375 A1 | 11/2010 | Friesen et al. | |

(Continued)

FOREIGN PATENT DOCUMENTS

| | | | |
|---|---|---|---|
| CN | 102 050 788 A | 5/2011 | |
| DE | 102008031480 A1 * | 1/2010 | ........... C07D 239/06 |

(Continued)

OTHER PUBLICATIONS

Machine Translation of: JP 2005/026023 A, Kuboki et al., Jan. 27, 2005.*

(Continued)

*Primary Examiner* — Kenneth Douyette
(74) *Attorney, Agent, or Firm* — Pillsbury Winthrop Shaw Pittman, LLP

(57) ABSTRACT

Embodiments are related to ionic liquids and more specifically to ionic liquids used in electrochemical metal-air cells in which the ionic liquid includes sulfonate ions as the anion.

12 Claims, 1 Drawing Sheet

(56) References Cited

U.S. PATENT DOCUMENTS

| | | |
|---|---|---|
| 2010/0323249 A1 | 12/2010 | Fujiwara et al. |
| 2011/0027664 A1 | 2/2011 | Burchardt |
| 2011/0027666 A1 | 2/2011 | Burchardt et al. |
| 2011/0152292 A1* | 6/2011 | Rayner-Branes et al. .... 514/256 |

FOREIGN PATENT DOCUMENTS

| | | |
|---|---|---|
| EP | 1 182 196 A1 | 2/2002 |
| EP | 1 398 318 A1 | 3/2004 |
| GB | 1 297 955 A | 11/1972 |
| JP | 2005 026023 A | 1/2005 |
| WO | 2010136783 A1 | 12/2010 |

OTHER PUBLICATIONS

Thomas Weldon, "Room-Temperature Ionic Liquids. Solvents for Synthesis and Catalysis", Chem. Rev. 1999, 99, 2071-2083.*

Wang, X., et al., "A polytetrafluoroethylene-quaternanry 1,4-diazabicyclo-[2.2.2]-octane polysulfone composite membrane for alkaline anion exchange membrane fuel cells", Intl. J. Hydrogen Energy, vol. 36 No. 16, pp. 10022-10026 (May 9, 2011).

Yan, X., et al., "Quaternized poly(ether ether ketone) hydroxide exchange membranes for fuel cells", J. Membrane Science, vol. 375, No. 1, pp. 204-211 (Mar. 22, 2011).

Stoica et al, "Anionic membrane based on polyepichlorhydrin matrix for alkaline fuel cell: Synthesis, physical and electrochemical properties", vol. 53, No. 4, pp. 1596-1603 (Oct. 30, 2007).

Park, J-S., "Development of Solid-State Alkaline Electrolytes for Solid Alkaline Fuel Cells", Macromolecular Symposia, vol. 249-250, No. 1, pp. 174-182 (Apr. 1, 2007).

Gu, S., et al., "Soluble and Highly Conductive Ionomer for High-Performance Hydroxide Exchange Membrane Fuel Cells", Angewandte Chemie Intl. Ed., vol. 48, No. 35, pp. 6499-6501 (Aug. 17, 2009).

Intl. Search Report/Written Opinion dated Dec. 3, 2012 of PCT/US2012/043000 filed Jun. 18, 2012 (15 pages).

Intl Search Report dated Nov. 28, 2012 of PCT/US2012/043013 dated Jun. 18, 2012 (15 pages).

Yao, C., et al., "Retention characteristics of organic compounds on molten salt and ionic liquid-based gas chromatography stationary phases", Journal of Chromatography, vol. 1216, No. 10, pp. 1658-1712 (Mar. 6, 2009).

Intl. Search Report/Written Opinion dated Sep. 5, 2012 of PCT/US2012/033940 filed Apr. 17, 2012 (11 pages).

Intl Search Report/Written Opinion of PCT/US2012/042955 filed Jun. 18, 2012 dated Sep. 6, 2012 (8 pages).

Intl. Preliminary Report on Patentabiliy dated Jun. 27, 2013 of PCT/US12/42955 filed Jun. 18, 2012 (12 pages).

Sharma, N. K., et al., "Do ion functional groups affect IL solvent properties? The case of sulfoxides and sulfones", Chem. Commun., pp. 646-648 (2006).

Terayama, Y., et al., "Well-Defined Poly(sulfobetaine) Brushes Prepared by Surface-Initiated ATRP Using a Fluoroalcohol and Ionic Liquids as the Solvents", Macromolecules, vol. 44, pp. 104-111 (2011).

Thielen, J., et al., "Model Compounds Based on Cyclotriphosphazen and Hexaphenylbenzene with Tethered Li—Solvents and Their Ion-Conducting Properties", Chem. Mater., vol. 23, pp. 2120-2129 (2011).

Zhao, C., et al., "Electrochemistry of Room Temperature Protic Ionic Liquids", J. Phys. Chem. B, vol. 112, pp. 6923-6936 (2008).

Goodrich, B. F., et al., "Effect of Water and Temperature on Absorption of $CO_2$ by Amine-Functionalized Anion-Thethered Ionic Liquids", J. Phys. Chem B, (Jun. 8, 2011).

Office action in related U.S. Appl. No. 13/526,058 dated Jul. 18, 2013.

* cited by examiner

IONIC LIQUID CONTAINING SULFONATE IONS

This invention was made with U.S. government support under Contract No. DB-AR-00000038 awarded by the Department of Energy. The government has certain rights in the invention. This application claims priority to provisional application 61/498,308 filed Jun. 17, 2011, the disclosure of which is incorporated herein by reference in its entirety.

FIELD OF THE INVENTION

Embodiments of the invention are related to ionic liquids and more specifically to ionic liquids used in electrochemical metal-air cells in which the ionic liquid includes sulfonate ions.

BACKGROUND

A significant detriment to the energy density of most batteries is posed by the battery's cathode. This is true for battery chemistries using, for example, lithium or nickel. Typically, oxidant is stored at the cathode at a molar charge capacity that is two to five times lower than that of the anode. Many fuel cells, on the other hand, use oxygen from the air as a source of oxidant. The existence of a continuous and virtually limitless oxidant source enables, in principle, high energy density. However, the use of hydrogen and organic fuels precludes high energy efficiencies due to problems with vapor pressure and balance-of-systems complexity, such as humidification and membrane issues. Metal-air electrochemical cells are able to combine the ultra-high anode capacity of batteries with the air-breathing cathode of fuel cells in order to achieve substantial energy densities that are relevant to modern energy demands.

Metal-air batteries typically include a fuel electrode at which metal fuel is oxidized, an air electrode at which oxygen is reduced, and an electrolyte for providing ion conductivity. A limiting factor with conventional metal-air batteries is the evaporation of the electrolyte solution (i.e., the ionically conductive medium), particularly the evaporation of the solvent, such as water in an aqueous electrolyte solution. Because the air electrode is required to be air permeable to absorb oxygen, it also may permit the solvent vapor, such as water vapor, to escape from the cell. Over time, the cell becomes incapable of operating effectively because of the depletion of the solvent. Indeed, in many cell designs this evaporation issue renders the cell inoperable before the fuel is consumed. The evaporation issue is exacerbated in secondary (i.e., rechargeable) cells, because the fuel may be re-charged repeatedly over the life of the cell, whereas the electrolyte solution cannot (absent replenishment from an external source).

There are other problems associated with conventional aqueous electrolyte batteries, such as water electrolysis during recharging, and self discharge. During recharge, a current is passed through the battery to reduce the oxidized fuel at the fuel electrode. Some of the current, however, electrolyzes the water resulting in hydrogen evolution (reduction) at the fuel electrode and oxygen evolution (oxidation) at the oxygen electrode as represented in the following equations:

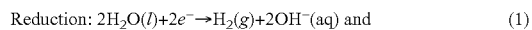

Reduction: $2H_2O(l) + 2e^- \rightarrow H_2(g) + 2OH^-(aq)$ and (1)

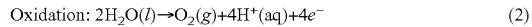

Oxidation: $2H_2O(l) \rightarrow O_2(g) + 4H^+(aq) + 4e^-$ (2)

In this manner, further aqueous electrolyte is lost from the battery. Additionally, the electrons that are consumed in reducing hydrogen are not available to reduce the fuel oxide. Therefore, the parasitic electrolysis of the aqueous electrolyte reduces the round trip efficiency of the secondary battery.

Self-discharge may result from impurities in the electrodes or reaction with the electrolyte. Typically, self-discharge from impurities in the electrodes is small (2-3% loss per month). The reaction of an active metal with water and/or $O_2$ dissolved in the water, however, may be quite high (20-30% per month).

To compensate for these problems, metal-air batteries with aqueous electrolyte solutions are typically designed to contain a relatively high volume of electrolyte solution. Some cell designs even incorporate means for replenishing the electrolyte from an adjacent reservoir to maintain the electrolyte level. However, either approach adds to both the overall size of the cell, as well as the weight of the cell, without enhancing the cell performance (except to ensure that there is a significant volume of electrolyte solution to offset evaporation of the water or other solvent over time). Specifically, the cell performance is generally determined by the fuel characteristics, the electrode characteristics, the electrolyte characteristics, and the amount of electrode surface area available for reactions to take place. But the volume of electrolyte solution in the cell generally does not have a significant beneficial effect on cell performance, and thus generally only detracts from cell performance in terms of volumetric and weight based ratios (power to volume or weight, and energy to volume or weight). Also, an excessive volume of electrolyte may create a higher amount of spacing between the electrodes, which may increase ohmic resistance and detract from performance.

The use of non-aqueous systems for electrochemical cells has been suggested (see e.g., U.S. Pat. No. 5,827,602). In non-aqueous systems, the aqueous electrolyte may be replaced with an ionic liquid. Ionic liquids which contain a strong Lewis acid such as AlCl3, however, are known to liberate toxic gases when exposed to moisture.

The use of low or room temperature ionic liquid rather than an aqueous electrolyte in a metal-air electrochemical cell, as described in U.S. Provisional Application Ser. No. 61/383, 510, filed Sep. 16, 2010; 61/355,081, filed Jun. 15, 2010; 61/334,047, filed May 12, 2010; 61/329,278, filed Apr. 29, 2010; 61/177,072, filed May 11, 2009, and 61/267,240, filed Dec. 7, 2009, and described in U.S. patent application Ser. No. 13/105,794, filed on May 11, 2011; Ser. No. 13/096,851, filed Apr. 28, 2011; Ser. No. 13/085,714, filed Apr. 13, 2011; and Ser. No. 12/776,962, filed May 10, 2010, the disclosures of each of which are incorporated herein by reference in their entirety. The use of a low or room temperature ionic liquid in the cell essentially eliminates the problems associated with evaporation of solvent from an electrolytic solution.

Blomgren et al. describe the use of ionic liquids as electrolyte materials in the lithium-ion battery (A. Webber, G. E. Blomgren, Advances in Lithium-Ion Batteries (2002), 185-232; G. E. Blomgren, J. Power Sources 2003, 119-121, 326-329). Covalent Associates in WO 01/93363 describe a non-flammable electrolyte consisting of a salt having an organic cation or of an ionic liquid, an organic solvent, an acrylate polymer or fluoropolymer, and a conducting salt. Yuasa Corporation in JP 2002373704 describes a non-aqueous electrolyte consisting of 1-ethyl-3-methylimidazolium, a lithium salt and a cyclic ester having a .pi. bond. Mitsubishi Chemicals Industries Ltd. in JP 11307121 describes an electrolyte consisting of an ionic liquid based on quaternary imidazolium or pyridinium ions and from 1% to 130% by volume of an organic cyclic compound. Jost, et al., U.S. Pat. No. 7,960,061 discloses ionic liquids for use as an electrolyte material, the disclosure of which is incorporated herein by reference in its entirety.

Sulfonate ion-containing compounds are known in the art. Numerous buffers known as Good's buffers contain sulfonate ions. Some ionic liquids are known to contain certain sulfonate (alkyl or aralkyl) ions such as trifluoromethylsulfonate. Sulfonate ions having longer alkyl chains, substituted with amines or heteroaromatic groups are not believed to have been described in the literature as useful anions in ionic liquids that are useful in electrochemical cell applications.

Room temperature ionic liquids have extremely low vapor pressures (some have vapor pressures that are essentially immeasurable under standard conditions) and thus experience little or no evaporation. Therefore, cells using low or room temperature ionic liquids as their ionically conductive media need not incorporate excessive volumes of solution in order to compensate for evaporation over time. Relatively small amounts of ionic liquid are sufficient to support the electrochemical reactions needed for cell operation, thereby reducing cell weight and volume and increasing power to volume/weight ratios. Also, other problems associated with solvents, such as hydrogen evolution in an aqueous solution, may be avoided. This inventive development is not conceded to be prior art and merely is described for contextual purposes to facilitate an understanding of the further development described herein.

SUMMARY

An embodiment of the invention relates to an ionic liquid comprising a sulfonate ion having the formula R—SO3-, wherein R is a substituted or unsubstituted alkyl group having $C_2$-$C_{20}$ carbon atoms, which together may form a ring, and a cation. An additional embodiment of the invention relates to a metal-air cell comprising a fuel electrode for oxidizing a fuel, an air electrode configured to absorb and reduce gaseous oxygen, and an ionic liquid comprising a sulfonate ion having the formula R—$SO_3^-$, wherein R is a substituted or unsubstituted alkyl group having $C_2$-$C_{20}$ carbon atoms, which together may form a ring, and a cation. Another embodiment of the invention relates to the ionically conductive medium per se for use in an electrochemical cell.

Other objects, aspects, and advantages of the present invention will become apparent from the following detailed description, the accompanying drawings, and the appended claim.

BRIEF DESCRIPTION OF THE DRAWINGS

The invention may best be understood by referring to the following description and accompanying drawings that are used to illustrate embodiments of the invention.

DETAILED DESCRIPTION

Figure 1:
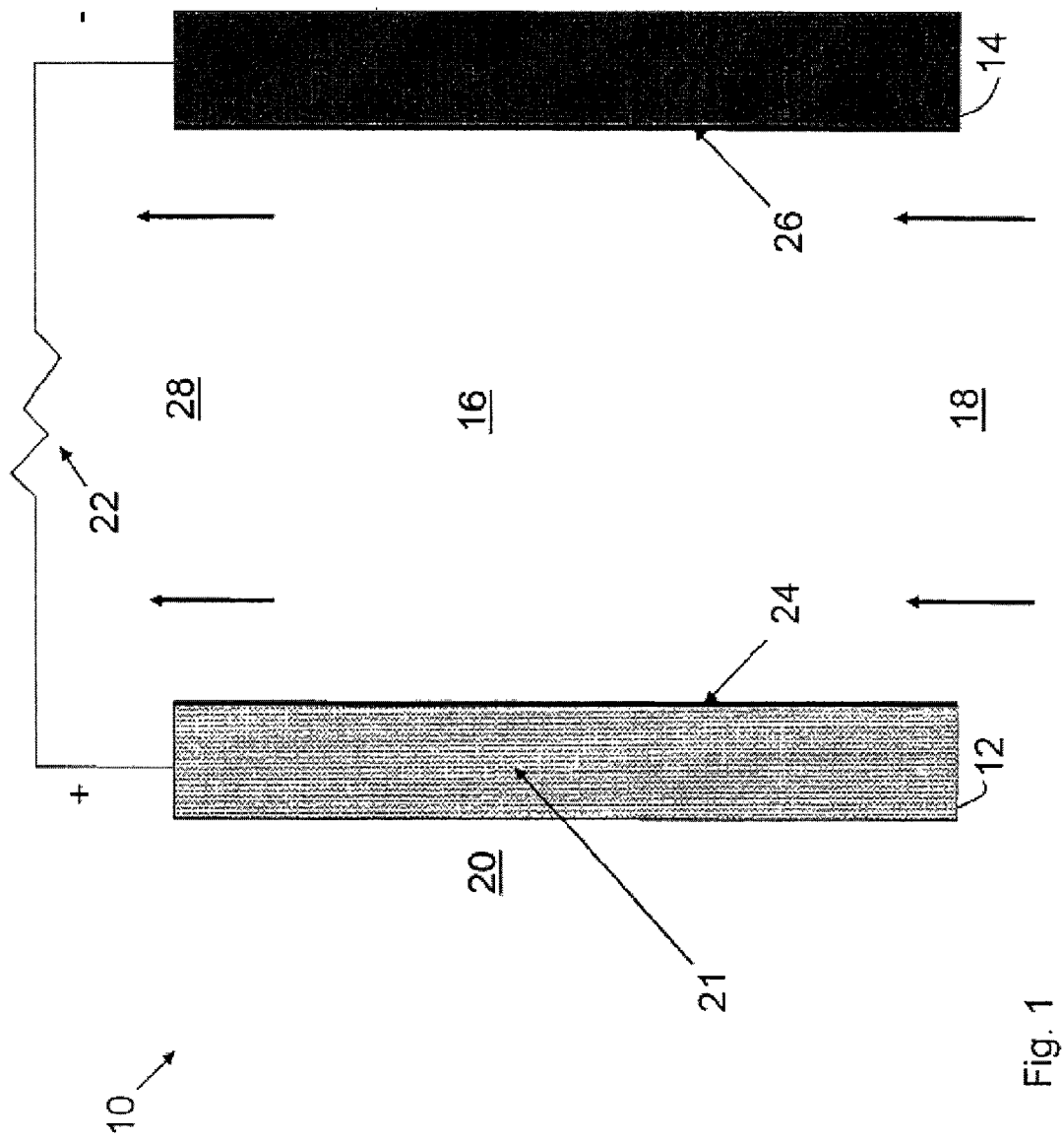
FIG. 1 is a schematic diagram of an electrochemical cell according to an embodiment of the invention.

For the purposes of this application, a low temperature ionic liquid is defined as an ionic liquid having a melting point at or below 150° C. at 1 atm. These low temperature ionic liquids may also include the species known as room temperature ionic liquids, which are defined as ionic liquids having a melting point at or below 100° C. at 1 atm. Ionic liquids are also referred to as liquid salts. By definition, an ionic liquid is composed primarily of anions and cations of the salt. While an ionic liquid itself may be a solvent with respect to one or more other soluble products present in the ionic liquid, such as an additive or reactant by-product created by operation of the cell, an ionic liquid does not require the use of a solvent to dissolve the salt, as the liquid itself is "self-dissolving," i.e., it is a liquid of the electrolyte salt anions and cations by its own nature, and the use of a separate solvent to dissolve the salt is not needed.

However, even though low temperature or room temperature ionic liquids are defined by their respective melting points at 1 atm., in some embodiments the cell may be operated in an environment with a different pressure, and thus the melting point may vary with the operating pressure. Thus, reference to a melting point at 1 atm. is used as a reference point to define these liquids, and does not imply or restrict its actual use conditions in operation. Reference to ambient conditions refers to 1 atm. pressure and room temperature.

In some non-limiting embodiments, a substance that may be regarded in some contexts as a solvent may be added in relatively small amounts to the ionic liquid, either for enhancing the solubility of solutes in the ionic liquid, such as an additive added to or a by-product created in the ionic liquid by operation of the cell, or for providing a non-solvent functionality, such as the promotion of certain electrochemical reactions or transport of ions. Thus, the use of an ionic liquid does not entirely exclude the presence of a substance that may be regarded as solvent in other contexts, or act as a solvent with respect to solutes in the ionic liquid, but because a solvent is not needed to dissolve an ionic liquid, it can be used in a substantially smaller amount compared to conventional electrolyte salts requiring a bulk solvent for dissolution of the salt per se, such as aqueous electrolyte solutions. Indeed, in some non-limiting embodiments it is possible that no additive solvent is used.

In some non-limiting embodiments, the ionically conductive medium between the fuel and air electrodes may be a pure low temperature ionic liquid, i.e., it consists of the ionic liquid. In other non-limiting embodiments, it may consist essentially of the ionic liquid, meaning for the purposes of this application that it may include the ionic liquid and one or more other substances that do not materially affect its characteristic of being an ionic liquid. Thus, the term "consisting essentially of" an ionic liquid expressly encompasses the addition of one or more additives to enhance the ionic transport functionality of the ionic liquid, support the electrochemical reactions of the cell and/or enhance the solubility of solutes in the ionic liquid, but excludes the use of a bulk solvent required to dissolve the salt, such as is the case with aqueous electrolyte solutions. Of course, any presence of reaction by-products or ions in the ionic liquid would be permitted in either the embodiments consisting of the ionic liquid or the embodiments consisting essentially of the ionic liquid, as the very nature of the ionic liquid is to promote the transport and/or formation of such ions and/or by-products. The terms "solvent free" or "devoid of solvent" may be used to characterize the ionic liquid, and this terminology should be understood as (a) only excluding a bulk solvent that is provided for purposes of dissolving the ionic liquid, and not excluding the ionic liquid itself, which may act as a solvent with respect to another substance (e.g., an additive or the cell reaction by-products); and (b) not excluding the presence of one or more additives to enhance the ionic transport functionality of the ionic liquid, support the electrochemical reactions of the cell and/or enhance the solubility of solutes in the ionic liquid, even if such an additive theoretically could be regarded as a solvent in other contexts or with respect to solutes in the ionic liquid, but is not functioning for purposes of dissolution of the ionic liquid. For example, in some embodiments, water may be present at a level between 10 ppm and 95 wt %, or from 50 ppm and 75 wt %, or from 75 ppm and 50 wt %, or less than 50 wt % to support electrochemical reactions even though it is not functioning as a solvent with respect to the ionic liquid as it would in other types of electrolytes, namely aqueous electrolytes.

Ionic liquids generally refer to salts that form stable liquids comprising ions. That is, ionic liquids are fully dissociated, consisting essentially of negative and positive ions. Thus, ionic liquids inherently conduct electricity. Further, ionic liquids have negligible vapor pressure, low viscosity, wide liquids (up to 400° C.), high thermal stability, and a large electrochemical window (>5V). Because of these properties, ionic liquids typically will not evaporate or be consumed during the charge/discharge cycle of an electrochemical cell.

Ionic liquids generally exist in two forms: protic and aprotic. Protic ionic liquids have available protons which may be oxidized or reduced or may coordinate with negative ions, such as reduced oxygens. Some examples of protic ILs are synthesized from combinations of anions tetrachloroaluminate, bis(trifluoromethylsulfonyl)imide, methylsulfonate, nitrate, and acetate, and cations triethylammonium, diethylmethylammonium, dimethylethylammonium, dimethylethylammonium triflate, ethylammonium, α-picolinium, pyridinium, and 1,8-bis(dimethylamino)naphthalene, 2,6-di-tert-butylpyridine, and derivatives of the guanadines. Aprotic ionic liquids, however, generally do not have proton activity. Some example of aprotic room temperature ionic liquids are synthesized from combinations of anions selected from chloride ($Cl^-$), hexafluorophosphate ($PF_6^-$), iodide, tetrfluorborate, bis(trifluoromethylsulfonyl)imide ($C_2F_6NO_4S_2^-$) (TFSI), trifluoromethanesulfonate ($CF_3O_3S^-$), and cations selected from imidazolium, sulfonium, pyrrolidinium, quaternized ammonium or phosphonium and their derivatives. Despite a lack of proton activity, an aprotic ionic liquid can comprise a proton. For example, an aprotic ionic liquid can comprise at least one cation that has at least one strongly bound proton thereto. Many other options of ionic liquids exist, and these lists of examples are not intended to be limiting in any way.

Embodiments of the invention include ionic liquids that have a vapor pressure at or below 1 mm Hg at 20° C. above its melting point, and preferably at or below 0.1 mmHg or zero or essentially immeasurable at 20° C. above its melting point. Room temperature ionic liquids ("RTIL") are salts that form a stable liquid at 100° C. or below at 1 atm. pressure (i.e., they have a melting point at 100° C. or below at 1 atm.). For the purposes of this application, a low temperature ionic liquid is defined as an ionic liquid having a melting point at or below 150° C. at 1 atm. Low temperature ionic liquids may also include the RTIL species.

However, even though low temperature or room temperature ionic liquids are defined by their respective melting points at 1 atm., in some embodiments the cell may be operated in an environment with a different pressure, and thus the melting point may vary with the operating pressure. Thus reference to a melting point at 1 atm. is used as a reference point to define these liquids, and does not imply or restrict its actual use conditions in operation.

The pH of a metal-air cell generally tends upward while cycling, and depending on the state of charge of the cell, organic components of an electrolyte may be exposed to superoxide, peroxidate, hydrogen peroxide, or other corrosive species. Few, if any, of both the cations (e.g., 1,3-dialkylimidazolium and N,N-dialkylpyrrolidinium) and anions (e.g., triflate and tfsi) prevalent in IL chemistry possess the stability to these conditions that are typically present in a commercialized metal-air cell.

Meanwhile, cations which one skilled in the art should anticipate would possess better-than-average stability to these conditions are either poorly described or heretofore unknown in the body of IL literature. For example, 1-methyl-1,4-diazabicyclo[2.2.2]octanium ([$C_1$ted]), 1-ethyl-2,3-dimethylimidazolium ([$C_2$dmim]), and tetramethylammonium ([TMA]) are less well explored as IL cations than, e.g., the 1,3-dialkylimidazolium and N,N-dialkylpyrrolidinium cations. Another, the imidazo[1,2-a]pyridinium cation is useful as an IL cation in the embodiments. In spite of the desirable chemical properties of these cations, they are generally unwieldy as electrolytes because, with the exception of [$C_2$dmim], they generally form undesirably high melting salts when paired with known IL anions (e.g., triflate, tfsi, methanesulfonate). This propensity is likely one of the reasons ILs based on these cations have not been developed extensively. Dicyanamide ([dca]) is one of the few exceptional anions with which these cations give rise to ILs when paired.

The embodiments described herein improve this situation in the first place by widening the field of available ions confirmed to give rise to ILs. The embodiments are desirable because they surprisingly and advantageously provide bona fide IL formulations even of the generally unwieldy cations listed above. The embodiments are additionally useful because these ILs may serve as non-aqueous bulk solvents for other ILs that, e.g., have a disadvantageously high melting point for commercial application to an electrochemical cell, or which are not desired as the only component of the electrolyte in an electrochemical cell. Moreover, the formulations of the embodiments generally retain the wide electrochemical window provided by the more ubiquitous IL ions, and in some cases offer even wider electrochemical windows.

Embodiments of the invention include ionic liquids comprising an anion having the formula $R-SO_3^-$, wherein R is a substituted or unsubstituted alkyl group having $C_2$-$C_{20}$ carbon atoms, which together may form a ring. Unsubstituted n-alkylsulfonates are known as IL anions, and in some embodiments are specifically excluded from the present invention. Suitable sulfonates for use in the preferred embodiments include, for example, isethionate ([ise]), taurinate ([tau]), and Good's buffers and the like (e.g., 3-morpholinopropanesulfonate (MOPS), 4-(2-hydroxyethyl)-1-piperazinepropanesulfonate (HEPPS, EPPS), 1,4-piperazinediethanesulfonate (PIPES), N-(2-acetamido)-2-aminoethanesulfonate (ACES), N-cyclohexyl-3-aminopropanesulfonate (CAPS), 4-(2-hydroxyethyl)-1-piperazineethanesulfonate (HEPES), 2-[(2-hydroxy-1,1-bis(hydroxymethyl)ethyl)amino]ethanesulfonate (TES), N-[tris(hydroxymethyl)methyl]-3-aminopropanesulfonate (TAPS), 3-(N-tris[hydroxymethyl]methylamino)-2-hydroxypropanesulfonate (TAPSO).

Isethionate, or 2-hydroxyethanesulfonate, ($C_2H_6O_4S$) is a known ion, the sodium salt of which is commonly used in detergent bar soaps and shampoos. Pentamidine isethionate is a known antimicrobial agent. It has not heretofore been known that isethionate could form an ionic liquid, much less be useful in a metal-air battery as an ionic conductive liquid. Indeed, due to the nature of isethionate being charge dense, hard, and having the additional capacity to hydrogen bond compared to n-alkylsulfonates, it would not have been expected that isethionate would be capable of forming a stable, much less useful ionic liquid. The discovery of isethionate as a stable and useful ionic liquid therefore is an unexpected discovery.

Taurinate is known to be useful with magnesium to protect against cardiac arrhythmia, and can be found in holistic medicines. Taurine is one of the few known naturally occurring sulfonic acids. It has not heretofore been known that taurinate could be useful as an anion in an ionic liquid, and for reasons exactly analogous to the isethionate case, it would not have been expected that taurinate would be capable of forming a stable, much less useful ionic liquid.

3-morpholinopropanesulfonate (MOPS) also is a known Good's buffer, a buffer introduced by Good, et al., in the 1960's. Good, Norman E.; et al., "Hydrogen Ion Buffers for Biological Research," *Biochemistry* 5 (2), pp 467-77 (1966). These buffers are well known to be useful in biological research and biochemistry, including its use in polyacrylamide gel electrophoresis. They and similar compounds are marked by heteroatom elaborations to alkylsulfonates. Other known Good's buffers and similar compounds useful in the preferred embodiments include 2-(N-morpholino)ethanesulfonate (MES), 4-(2-hydroxyethyl)-1-piperazineethanesulfonate (HEPES), 3-[4-(2-hydroxyethyl)-1-piperazine] propanesulfonate (HEPPS), N-cyclohexyl-3-aminopropanesulfonate (CAPS), N-cyclohexyl-2-aminoethane sulfonate, 3-{[tris(hydroxymethyl)methyl] amino}propane sulfonate (TAPS), 3-[N-Tris{hydroxymethyl)methylamino]-2-hydroxypropane sulfonate (TAPSO), 2-{[tris(hydroxymethyl)methyl] amino}ethane sulfonate (TES), piperazine-N,N'-bis(2-ethanesulfonic acid) (PIPES), and the like. The chemical formula for these buffers are shown below, in which the corresponding sulfonate anion is formed by removal of the hydrogen on the OH:

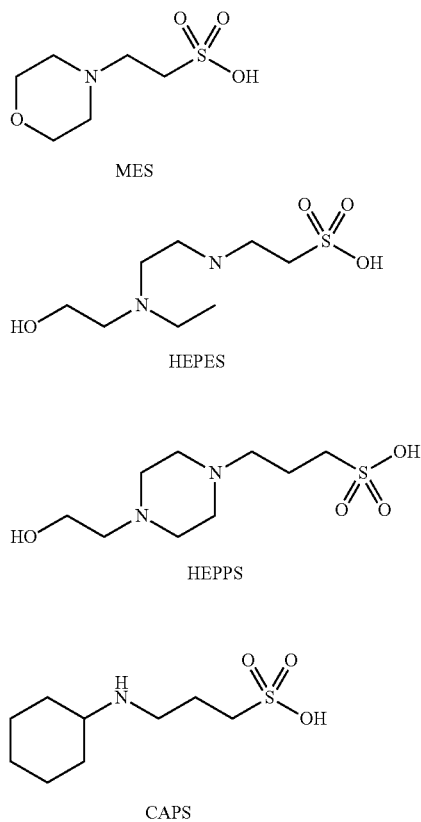

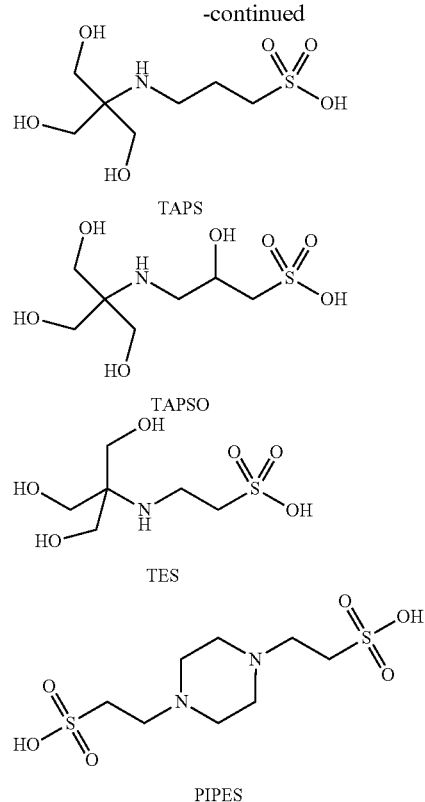

The ionic liquids of the embodiments include the sulfonate ions described above, together with a suitable cation. Any cation may be used in the embodiments so long as it forms an electrically conductive ionic liquid with the sulfonate anion. Suitable cations are those containing tertiary nitrogens that have been quaternized and subsequently converted into the corresponding positive ion. Some representative cations include, but are not limited to pyrrolidines, piperidines, imidazoles, pyridines, morpholines, and the like. Particularly preferred cations are 1-alkyl derivatives of 1,4-diazabicyclo [2.2.2]octane (also known as triethylenediamine, ted, or DABCO®) (DABCO® is a registered trademark for Air Products' catalyst product line including 1,4-diazabicyclo [2.2.2]octane), and especially 1-methyl-1,4-diazabicyclo [2.2.2]octanium, 1-ethyl-2,3-dimethylimidazolium, N-ethyl-N-methylmorpholinium, 1-methylimimdazo[1,2-a] pyridinium, tetramethylammonium, and the like. Those skilled in the art, using the guidelines provided herein, will be capable of providing a suitable cation to the sulfonate anion to produce a suitable ionic liquid.

In a zinc-air battery using ionic liquid electrolytes, the water content is typically controlled to minimize hydrogen evolution, control plating morphology, and maintain a constant water activity within the cell. On discharge, Zn metal is oxidized at the fuel electrode and solvated or complexed into solution, releasing electrons into the circuit. Simultaneously, molecular oxygen is reduced at the air electrode consuming those electrons released at the anode. Upon reaching the solubility of zinc ions, ZnO is precipitated within the cell. On charge, $Zn^{2+}$ ions are reduced at the negative (fuel) electrode. Simultaneously at the air electrode, an oxidation reaction that results in the evolution of molecular oxygen occurs.

In aqueous metal-air batteries the oxidation reaction at the air electrode during charge is simply the oxidation of water.

This reaction, in addition to releasing $O_2$ gas, results in $H^+$ ions migrating through the cell. However, because zinc has a large overpotential for the hydrogen reduction reaction in aqueous electrolytes, faradaic efficiencies on the of order 95% are seen. The faradaic or current efficiency is the efficiency with which charge (electrons) are transferred in an electrochemical system. Electron losses are generally caused by electrons which participate in unproductive reactions and short circuits. Hydrogen reduction is an example of such an unproductive reaction. Thus, the large overpotential for hydrogen reduction (i.e., the barrier which must be overcome for hydrogen reduction) on zinc means that hydrogen reduction is unfavorable, resulting in a high faradaic efficiency.

Certain ionic liquids useful in the preferred embodiments allow anywhere from 0.1-50% (or even higher) water into a zinc-air ionic liquid battery, the oxidation reactions at the air electrode during charge are supported—that is, water is made available at the oxygen electrode for oxidation. Additionally, small quantities of water within ionic liquids destabilize the well known superoxide species ($HO_2$) that is generated in aprotic media, high pKa conjugate acids, and basic media via disproportionation reactions.

An additional benefit to adding water to the ionic liquid is that the $H^+$ ions released from the water oxidation reaction transiently mildly acidify the electrolyte thereby promoting the solvation of the ZnO precipitate. More specifically, the $H^+$ ion may increase acidity local to the ZnO precipitate, but may not acidify the solution on a bulk scale. The solvation of ZnO can be described in the following reaction:

$$ZnO + 2H^+ \rightarrow Zn^{2+} + H_2O \qquad (3)$$

Further, small quantities of water in ionic liquids may substantially decrease viscosity, resulting in an increase in conductivity.

In addition, the faradaic efficiency in aqueous electrolytes is high (~95%). This is true even without the specific adsorption of ionic liquid ions (or additives within the cell). Because of the high faradaic efficiency in aqueous electrolytes, an ionic liquid electrolyte with a 5% water content is expected to have a faradaic loss on the order of 0.25% (5% water content*5% loss=0.25%).

In a metal-air battery, the metal is the fuel. That is, during discharge the metal is oxidized at the anode, providing electrons which can be used for electrical work. The oxidation reaction may be represented by the following equation:

$$\text{Metal} \rightarrow \text{Metal}^{n+} + (n)e^- \qquad (3)$$

The metal fuel may be of any type, and may be electrodeposited, absorbed, physically deposited, or otherwise provided on or constituting the fuel electrode. The fuel may be of any metal, including alloys or hydrides thereof, for example. For example, the fuel may comprise transition metals, alkali metals, alkali earth metals, and other or "poor" metals. Transition metals include, but are not limited to zinc, iron, manganese, and vanadium. The most common alkali metal is lithium but other alkali metals may be used. The other metals include, but are not limited to magnesium, aluminum and gallium. As used herein, the term metal fuel refers broadly to any fuel comprising a metal, including elemental metal, metal bonded in a molecule or complex, including oxides, metal alloys, metal hydrides, etc. The fuel electrode may be formed of the metal fuel as the electrode body itself in some embodiments.

The fuel electrode may have any construction or configuration. For example, the fuel electrode may be a porous structure with a three-dimensional network of pores, a mesh screen, a plurality of mesh screens isolated from one another, or any other suitable electrode. The fuel electrode includes a current collector, which may be a separate element, or the body on which the fuel is received may be electroconductive and thus also be the current collector. In an embodiment, the fuel electrode is laminated, bonded, or attached to a backing that provides the external surface of the fuel electrode. This backing may be liquid impermeable or essentially impermeable to the ionic liquid to prevent the ionic liquid from permeating outwardly through the fuel electrode via its external surface. More preferably, the backing is also impermeable to air, and particularly oxygen or other oxidant, to prevent any undesirable parasitic reaction, such as oxidant reduction in the presence of the fuel oxidation that occurs at the electrode during discharge.

Further details regarding metal fuels and fuel electrodes may be found in U.S. patent application Ser. Nos. 12/385,217, 12/385,489, 12/885,268, 12/901,410, 12/631,484, 12/549, 617, 13/019,923, 13/028,496, 61/193,540, 61/301,377, 61/323,384, 61/329,278, 61/365,645, 61/394, 954, 61/358, 339, 61/383,510 and 61/243,970, the disclosures of each of which is incorporated by reference herein in their entirety.

During discharge, oxygen at the air electrode is reduced, consuming electrons. There are several possible mechanisms for oxygen reduction. The oxygen reduction reaction may occur, for example, via one of the three mechanisms discussed below. Other mechanisms, however, may occur depending on the chemical system (ionic liquid, electrode materials) chosen.

A first possible and non-limiting mechanism is a four-electron oxygen reduction reaction (ORR) where the product is a fully reduced oxygen dianion. The four-electron oxygen reduction reaction may be represented by the following equation:

$$O_2 + 2H_2O + 4e^- \rightarrow 4OH^- \qquad (4)$$

Depending on the specific chemistry of the system, this reaction may form a soluble product or result locally in the formation of an insoluble metal-oxide.

In this reaction, the anions liberated may serve to mediate continued anode reaction. Relative to the other oxygen reduction mechanisms, the four-electron oxygen reduction reaction has the advantages of increased energy density and extracting the maximum number of electrons per oxygen molecule.

A second possible and non-limiting mechanism is a two-electron peroxide route. An examples of this mechanism may be represented by the following equation:

$$Zn^{2+} + O_2 + 2e^- \rightarrow ZnO_2 \qquad (6)$$

This mechanism has the advantage of relatively low overpotentials for the peroxide reaction. It also tends to have enhanced rechargeability relative to the first mechanism. The two-electron peroxide mechanism, however, results in lower energy density at the oxygen electrode battery relative to a four-electron process.

A third possible and non-limiting mechanism is a mixed two-electron/four-electron ORR that capitalizes on the reducing power of certain aliovalent cations. An examples of this mechanism may be represented by the following equation:

$$Mn^{2+} + O_2 + 2e^- \rightarrow MnO_2 \qquad (7)$$

The nuance in this mechanism is that the product involves fully reduced $O^{2-}$ species generated by the reducing power of the aliovalent metal. In this example, $Mn^{2+}$ ends up in the $Mn^{4+}$ state on the right. This mechanism has the advantage of lower overpotentials due to reducing power of the aliovalent cation. Further, aliovalent metals may be used to make more efficient cells. The mixed two-electron/four-electron mechanism, however, results in a lower energy density battery relative to a four-electron process.

Air electrodes are typically porous structures made of polytetrafluoroethylene (PTFE) materials such as Teflon®. Preferably, the air electrode material has a high degree of solvophobicity with the electrolyte. Solvophobicity within the air electrode serves the dual roles of "wet-proofing" (i.e. preventing liquid electrolyte from leaving the cell) and improving access of the oxygen in the air to the oxygen reduction reaction catalyst within the porous structure. Access to the catalyst is enhanced by solvophobicity due to an increase in the triple-junction line length of air-catalyst-electrolyte. The increase in the triple-junction line length reduces transport limitations. While a strong solvophobic character is advantageous, however, including solvophilic constituents in the electrode improves the tortuosity of the triple junction, improving superficial reaction site density.

FIG. 1 illustrates a low temperature ionic liquid (IL) electrochemical cell ("electrochemical cell"), generally indicated at 10, according to the embodiments of the present invention. As illustrated and described below, the electrochemical cell 10 includes a plurality of electrodes including a first electrode 12 and a second electrode 14. In other embodiments, the first electrode or the second electrode of the electrochemical cell 10 may be provided by configurations other than a single electrode. In the non-limiting embodiment illustrated in FIG. 1, the first electrode 12 is a cathode, and more specifically an air cathode, and will be referred to hereinafter as an air electrode 12. The second electrode 14 is an anode, and will be referred to hereinafter as a metal electrode 14. In an embodiment, and as described below, the electrochemical cell 10 may generate electricity by virtue of an oxidation half-reaction of a fuel at the metal electrode 14 in parallel, that is, substantially at the same time, with a reduction half-reaction of an oxidizer 20 at the air electrode 12. The illustrated embodiment is not intended to be limiting in any way.

The air electrode 12 and the metal electrode 14 preferably are spaced apart to form a gap 16 therebetween. A room temperature ionic liquid (RTIL), generally indicated at 18, may flow along the gap 16 so that the RTIL 18 may contact both the air electrode 12 and the metal electrode 14 at the same time. In an embodiment, it should be understood that the electrochemical cell 10 may be oriented in any way, and the RTIL may flow in directions other than what is illustrated. Thus, any directional references are made with regard to the orientation as shown in FIG. 1, and are not intended to limit a working embodiment to any particular orientation. In other embodiments, the RTIL 18 may be static with no flow at all. The RTIL 18 may make contact with the air electrode 12 at an air electrode/RTIL interface 24. The RTIL 18 may make contact with the metal electrode 14 at a metal electrode/RTIL interface 26. In alternative embodiments, the RTIL does not flow. That is, no mechanism for forced flow is included in the cell.

It is preferred in certain embodiments that the RTIL contain water to facilitate the electrochemical reactions (discharging and charging over a number of cycles) taking place within the electrochemical cell 10. Preferably, the ionic liquid includes water in amounts of from about 15% to about 50%, more preferably from about 20% to about 40%, and most preferably from about 25% to about 30%. In electrochemical cells 10 that do not comprise a cathode and/or anode that requires water to facilitate the electrochemical reactions, it is preferred that the ionic liquids comprise less than about 25% water, more preferably less than about 20%, even more preferably less than about 15% water. Those skilled in the art will be capable of determining the appropriate amount of water to include in the RTIL prepared in accordance with the embodiments, using the guidelines provided herein.

As alluded to above, a reduction half-reaction may take place at the air electrode 12. In an embodiment, an oxidizer 20 may be reduced through the reduction half-reaction at the air electrode 12. For non-limiting illustration purposes, the electrons from the metal electrode 14 may flow to an external circuit 22 (i.e., a load) and return to the air electrode 12 to facilitate the reduction of the oxidizer 20. The oxidizer 20 is reduced on the air electrode 12 at oxidizer reduction reaction sites 21. In an embodiment, a catalyst is used to facilitate the oxidizer reduction half-reaction at the oxidizer reduction reaction sites 21. The air electrode 12 may include catalyst material, such as manganese oxide, nickel, pyrolyzed cobalt, activated carbon, silver, platinum, or any other catalyst material or mixture of materials with high oxygen reduction activity for catalyzing reduction of the oxidizer, which will be discussed below. In an embodiment, the air electrode 12 may be porous and the porous body with a high surface area may comprise the catalyst material.

In an embodiment, the air electrode 12 may be a passive or "breathing" air electrode 12 that is passively exposed, such as through windows or openings to an oxidizer source (typically oxygen present in ambient air) and absorbs the oxidizer 20 for consumption in the electrochemical cell 10 reactions. That is, the oxidizer 20, will permeate from the oxidizer source into the air electrode 12. Thus, the oxidizer 20 need not be actively pumped or otherwise directed to the air electrode 12, such as via an inlet. Any part of the air electrode 12 by which the oxidizer 20 is absorbed or otherwise permeates or contacts the air electrode 12 may be generically referred to as an "input." The term input may broadly encompass all ways of delivering oxidizer to the air electrode 12 for the oxidizer reduction half-reaction at the oxidizer reduction reaction sites 21 on the air electrode 12.

By means of a non-limiting illustration, the air electrode 12 may be a gas permeable electrode having an outer surface exposed to ambient air such that the oxidizer 20 comprises oxygen that permeates the air electrode 12. Similarly, the air electrode 12 may comprise a barrier membrane on the outer surface of the air electrode 12 that is gas permeable and liquid impermeable so as to permit permeation of the oxidizer 20 via the outer surface of the air electrode 12 and prevent the RTIL 18 from flowing through the outer surface of the air electrode 12. In an embodiment, the air electrode 12 may be a porous body covered on the inner side by a liquid permeable layer through which the RTIL 18 may pass through so that the low temperature IL 18 may contact the porous body.

The relationship between the RTIL 18 and the air electrode 12 may impact the overall energy density of the electrochemical cell 10. For that reason, the vapor pressure and surface tension characteristics of the RTIL 18 in view of the air electrode 12 should be carefully selected. For instance, in an embodiment, the air electrode 12 may repel the RTIL so that it may prevent the RTIL 18 from wicking, that is, flowing in a capillary-like manner through the air electrode 12. In another embodiment, the air electrode 12 may be designed with porosity to absorb the RTIL so that it exposes the RTIL to more air electrode 12 surface area for purposes of enabling the desired electrochemical reactions at the air electrode 12. The air electrode 12 may support catalyst decoration at the oxidizer reduction reaction sites 21 to improve the efficiency of the reaction. In an embodiment, the catalyst may be decorated with metal ions which may enhance the activity of the catalyst in catalyzing the oxidizer reduction reaction at the oxidizer reduction reaction sites 21 on the air electrode 12. The air electrode 12 may have a high ionic conductivity to provide reactants and remove products of the oxidizer reduction reaction from the air electrode 12. In an embodiment, the air electrode 12 may have high electrical conductivity character to carry electrons from the external load 22 to the oxidizer reduction reaction sites 21. The air electrode 12 and RTIL 18 characteristics may be further defined.

In an embodiment, the metal-oxide by-products 28 may be formed at the metal electrode 14. Whereas reduced oxidizer ions in an aqueous electrolyte coordinate, that is, donate electrons to water molecules to form water, peroxides and/or hydroxides, and thereby increase problems with vapor pressure and corrosion, in this non-limiting embodiment, the RTIL 18 may promote both the oxidizer reduction reaction at the air electrode 12 and the conduction of the reduced oxidizer ions to the metal electrode 14. In support of this result, the RTIL 18 may contain soluble species that interact with the reduced oxidizer ions, with the RTIL 18 typically being protic. The RTIL 18 may also support the reduced oxidizer ions as they migrate to the metal electrode 14. By means of a non-limiting illustration, the migration of the reduced oxidizer ions may refer to transport of the reduced oxidizer ions via convection transport, or conduction transport or diffusion transport. The RTIL 18 may also support the oxidized metal-fuel ions remaining at the metal electrode 14. In doing so, the RTIL 18 promotes the reaction between the reduced oxidizer ions and the oxidized metal-fuel ions to produce the metal-oxide by-products 28. In an embodiment, the metal-oxide by-products 28 may be stored at the metal electrode 14. In an embodiment where the metal-oxide by-product 28 is stored at the metal electrode 14, this embodiment is best used as a primary (i.e., non-rechargeable) battery, as the oxygen is stored at the metal electrode 14 and is not locally available to an oxygen evolving electrode for oxidation of the reduced oxygen species.

The storage of the metal oxide locally at the air electrode is facilitated by the air electrode 12 having a pore size in at least the regions contacting the ionic liquid sufficient to contain the oxide within the air electrode 12 body. That is, the pore size may be dependent on the size of the oxide. A network of such pores may increase the storage capacity of the air electrode 12.

In an embodiment, the oxidizer source is ambient air, and the oxidizer 20 is oxygen. In an embodiment, oxygen as the oxidizer 20 may be reduced at the air electrode 12 to form reduced oxygen ions. In an embodiment, the oxygen may be supplied from an evolved oxygen recovery system used in a regenerative electrochemical cell. Other examples of electrochemical cells that may be useful embodiments of the invention herein are shown, for example, in U.S. patent application Ser. No. 12/549,617, filed on Aug. 28, 2009, which is incorporated herein by reference in its entirety.

The electrolytes of the embodiments may be used in other cell configurations. An alternate cell configuration, for example, comprises a compact wound cell illustrated in U.S. Patent Application No. 61/267,240 and Ser. No. 12/776,962, hereby incorporated by reference in their entirety.

Because of evaporation, water electrolysis during recharging, and self-discharge, aqueous electrolytes can be problematic for metal air batteries. These problems not only result in a loss of electrolyte but also a reduction in the round trip efficiency of a rechargeable battery. The use of an ionic liquid electrolyte reduces or may eliminate some of these problems. Even with an ionic liquid electrolyte, however, the presence of water may cause the release of toxic gases and/or cause self-discharge. On the other hand, an ionic liquid electrolyte according to embodiments of the invention may include small amounts of water. For example, water contents of 10-100 ppm have been found to improve oxygen reduction of aprotic systems without causing unacceptable self-discharge or release of toxic gases. Consequently, some embodiments include ionic liquids prepared as described herein, in which the ionic liquids contain anywhere from about 5 to about 100,000 ppm water, more preferably from about 7 to about 1,000 ppm water, and most preferably from about 10 to about 100 ppm water. In some embodiments, water may be present at a level between 10 ppm and 95 wt %, or from 50 ppm and 75 wt %, or from 75 ppm and 50 wt %, or less than 50 wt % to support electrochemical reactions even though it is not functioning as a solvent with respect to the ionic liquid as it would in other types of electrolytes.

All publications, patents, and patent applications cited herein are hereby incorporated by reference in their entirety.

The articles "a" and "an" are used herein to refer to one or to more than one (i.e., to at least one) of the grammatical object of the article. By way of example, "a polymer resin" means one polymer resin or more than one polymer resin. Any ranges cited herein are inclusive. The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

The following examples are provided for illustrative purposes only. Ionic liquids were prepared using various cations and various sulfonate containing anions. These ionic liquids were tested for stability and usefulness in an electrochemical cell. The results revealed that the ionic liquids would be useful as electrolytes in electrochemical cells.

EXAMPLES

The examples provided below are provided solely to illustrate the reaction principles of the embodiments and should not be regarded as limiting. To the contrary, the embodiments are intended to encompass all modifications, alterations, substitutions, and equivalents within the spirit and scope of the appended claims. In examples comprising Good's buffers and related compounds, the same abbreviations are used for each member of a conjugate acid-base pair. Persons having ordinary skill in the art will recognize from the context whether the Good's buffer or like compound exists as the acid or base conjugate Example 1

Preparation of [$C_1$ted][MOPS]

[$C_1$ted][MOPS] is an ionic liquid comprised of the cation, 1-methyl-1,4-diazabicyclo[2.2.2]octanium ([$C_1$ted]), and as the anion, 3-morpholinopropanesulfonate ([MOPS]).

A 21.859-g flask was loaded sequentially with MOPS (1.247 g, 5.96 mmol) and aqueous [$C_1$ted][OH] (0.92 M, 6.480 mL, 5.96 mmol). Water was removed by rotary evaporation to produce [$C_1$ted][MOPS] (1.996 g, 100%, nominally −0.15 wt % water) as a viscous, colorless ionic liquid. The ionic liquid of Example 1 was liquid at ambient conditions and had an electrochemical window of 7V with a platinum working electrode.

Example 2

Preparation of [$C_1$ted][TAPS]

[$C_1$ted][TAPS] is an ionic liquid comprised of $C_1$ted as the cation, and N-tris(hydroxymethyl)methyl-4-aminobutane sulfonic acid (TAPS) as the anion. A 5.4342-g vial was charged sequentially with TAPS (2.2398 g, 9.2 mmol) and aqueous [C$_1$ted][OH] (0.92 M, 10.0 mL, 10.1906 g, 9.2 mmol). The pH of the solution registered 9-10 on universal indicating pH paper. An aliquot (1.5984 g, 12.9%) was withdrawn and concentrated by rotary evaporation to produce [C$_1$ted][TAPS] (0.4786 g, >100%, nominally 8% water) as an ionic liquid. The ionic liquid of Example 2 was liquid at ambient conditions.

Example 3

Preparation of [C$_1$ted][ise]

[C$_1$ted][ise] is an ionic liquid comprised of C$_1$ted as the cation, and isethionate (ise) as the anion. A 138.662-g 1-neck bottom flask holding an aqueous solution of [C$_1$ted][OH] (0.832 M, 47 mL, 39 mmol) was fitted with a pH probe such that the probe extended below the level of the batch. The pH was adjusted from 13.71 to 4.96 by the addition of about 10 mL of 1.8 M sulfuric acid around the probe with stirring. The mixture was concentrated as far as feasible by rotary evaporation to leave an 8.632-g residue, nominally considered as [C$_1$ted]$_2$[SO$_4$] (6.853 g, 100%) and water (1.779 g). Reagent alcohol (4 mL) was added to this mixture, rendering it a solution of nominal [C$_1$ted]$_2$[SO$_4$] in 2:1 alcohol-water, whereupon sodium isethionate (5.869 g, 40 mmol) dissolved in a minimal amount of 2:1 alcohol-water (about 30 mL) was added. The resulting slurry was stirred for about 2 h, whereupon it was suction filtered, and the filtrate was concentrated as far as feasible by rotary evaporation. The residue was taken up in methanol (25 mL) and loaded onto an about 20-g column of 230-400 mesh silica gel previously packed in methanol.

The methanolic solution of crude [C$_1$ted][ise] was pushed down to the level of the top of the silica gel bed with air pressure while the column issue was collected in a 250-mL round bottom flask; the flask previously containing the crude product was rinsed with methanol (25 mL) and the rinse methanol was similarly loaded and pressed down while the column issue was collected on top of the first fraction. The rinsing process was repeated once before the silica gel column was washed down with fresh methanol (100 mL), all the while collecting the column issue on top of the accumulated methanol solution. The combined methanolic fractions were concentrated by rotary evaporation to produce purified [C$_1$ted][ise] (8.56 g, 34 mmol, 87%) as an ionic liquid The ionic liquid of Example 3 was liquid at ambient conditions and had an electrochemical window of 3V with a platinum working electrode.

Example 4

Preparation of [C$_2$dmim][ise]

[C$_2$dmim][ise] is an IL comprised of 1-ethyl-2,3-dimethylimidazolium as the cation, and isethionate (ise) as the anion. A 250-mL round bottom flask was charged with [C$_2$dmim]$_2$[SO$_4$] (7.331 g, 21 mmol) and 2:1 alcohol-water (24 mL). This mixture was stirred until forming a clear, colorless solution, whereupon a prepared solution of sodium isethionate (6.267 g, 42 mmol) was added to the mixture in one portion with stirring. A fine precipitate formed soon thereafter. The resulting slurry was stirred for about 2 h, whereupon it was suction filtered, and the filtrate was concentrated as far as feasible by rotary evaporation. The residue was taken up in methanol (25 mL) and loaded onto an about 20-g column of 230-400 mesh silica gel previously packed in methanol.

As in Example 3, the methanolic solution of crude [C$_2$dmim][ise] was pushed down to the level of the top of the silica gel bed with air pressure while the column issue was collected in a 250-mL round bottom flask; the flask previously containing the crude product was rinsed with methanol (25 mL) and the rinse methanol was similarly loaded and pressed down while the column issue was collected on top of the first fraction. The rinsing process was repeated once before the silica gel column was washed down with fresh methanol (100 mL), all the while collecting the column issue on top of the accumulated methanol solution. The combined methanolic fractions were concentrated by rotary evaporation to produce purified [C$_2$dmim][ise] (10.713 g, 43 mmol, 101%) as an ionic liquid. The ionic liquid of Example 4 was liquid at ambient conditions.

Example 5

[TMA][ise]

[TMA][ise] is an ionic liquid comprised of tetramethylammonium (TMA) as the cation, and isethionate (ise) as the anion. In a manner similar to Example 3, a 1-neck round bottom flask holding an aqueous solution of [TMA][OH].5 H$_2$O (9.094 g, 50 mmol) was fitted with a pH probe such that the probe extended below the level of the batch. The pH was adjusted from 14.68 to 5.49 by the addition of 1.44 M sulfuric acid (17.8 mL, 26 mmol) around the probe with stirring, whereupon sodium isethionate (7.438 g, 50 mmol) dissolved in a minimal amount of 2:1 alcohol-water (about 40 mL) was added. The resulting slurry was stirred for about 2 h, whereupon it was suction filtered, and the filtrate was concentrated as far as feasible by rotary evaporation. The residue was taken up in methanol (25 mL) and loaded onto an about 20-g column of 230-400 mesh silica gel previously packed in methanol.

As in Example 3, the methanolic solution of crude [TMA][ise] was pushed down to the level of the top of the silica gel bed with air pressure while the column issue was collected in a 250-mL round bottom flask; the flask previously containing the crude product was rinsed with methanol (25 mL) and the rinse methanol was similarly loaded and pressed down while the column issue was collected on top of the first fraction. The rinsing process was repeated once before the silica gel column was washed down with fresh methanol (100 mL), all the while collecting the column issue on top of the accumulated methanol solution. The combined methanolic fractions were concentrated by rotary evaporation to produce purified [TMA][ise] (10.098 g, 51 mmol, 102%) as an ionic liquid. The ionic liquid of Example 5 was solid at ambient conditions, liquid when contained in a sample vial immersed in an 80° C. water bath, and liquid in a relative humidity (RH) chamber maintained above ambient humidity but below 40% RH.

Example 6

[C$_1$ted][EPPS]

[C$_1$ted][EPPS] is an IL comprised of C$_1$ted as the cation, and 4-(2-hydroxyethyl)-1-piperazinepropanesulfonate (EPPS) as the anion. In a manner similar to the method of Example 2, a 5.0-g vial was charged sequentially with EPPS (2.3218 g, 9.2 mmol) and aqueous [C$_1$ted][OH] (0.92 M, 10.0 mL, 10.0643 g, 9.2 mmol). The pH of the solution registered 9-10 on universal indicating pH paper. An aliquot (1.5822 g, 12.8%) was withdrawn and concentrated by rotary evaporation to produce [C$_1$ted][EPPS] (0.4764 g, >100%, nominally 6% water) as an ionic liquid. The ionic liquid of Example 2 was liquid at ambient conditions. The ionic liquid of Example 6 was liquid at ambient conditions and had an electrochemical window of 3V with a platinum working electrode.

Example 7

[C$_1$ted][tau]

[C$_1$ted][tau] is an IL comprised of C$_1$ted as the cation and taurinate (tau) as the anion. In a manner analogous to the method in Example 1, a 21.908-g flask was loaded sequentially with taurine (0.996 g, 7.96 mmol) and aqueous [C$_1$ted][OH] (0.92 M, 8.649 mL, 7.94 mmol). Water was removed by rotary evaporation to produce [C$_1$ted][tau] (1.884 g, 94%, nominally ~6 wt % water) as a viscous, colorless ionic liquid. The ionic liquid of Example 7 was liquid at ambient conditions and had an electrochemical window of 5V with a platinum working electrode.

Example 8

[C$_1$ted][TAPSO]

[C$_1$ted][TAPSO] is an IL comprised of [C$_1$ted] as the cation and 3-[N-Tris(hydroxymethyl)methylamino]-2-hydroxypropanesulfonic acid ([TAPSO]) as the anion. In a manner analogous to the method in Example 1, a 135.148-g flask was loaded sequentially with TAPSO (6.7432 g, 26 mmol) and aqueous [C$_1$ted][OH] (0.8 M, 32.5 mL, 26 mmol). Water was removed by rotary evaporation to produce [C$_1$ted][TAPSO] (10.370 g, 95%, nominally ~5 wt % water) as a viscous, colorless ionic liquid. The ionic liquid of Example 8 was liquid at ambient conditions.

Example 9

[TMA][TAPSO]

[TMA][TAPSO] is an IL comprised of [TMA] as the cation and 3-[N-Tris(hydroxymethyl)methylamino]-2-hydroxypropanesulfonic acid ([TAPSO]) as the anion. In a manner analogous to the method in Example 1, a 64.125-g flask was loaded sequentially with TAPSO (3.1121 g, 12 mmol) and aqueous [TMA][OH] (4 M, 3 mL, 12 mmol). Water was removed by rotary evaporation to produce [TMA][TAPSO] (4.127 g, 97%, nominally ~3 wt % water) as a viscous, colorless ionic liquid. The ionic liquid of Example 9 was liquid at ambient conditions.

Example 10

Quaternary Mixture IL

A Quaternary Mixture IL comprised of [C$_1$ted] [MOPS] (Example 1), [C$_1$ted] [ise] (Example 3), and [C$_1$ted] [tau] (Example 7) which are known to make IL's as described herein, along with the electrochemically active anion [OH]. IL's were mixed to provide mixtures having properties such as lowered freezing temperature and decreased relative humidity of deliquescence. [C$_1$ted] [ise] was prepared as illustrated in Example 3 and used as an aqueous solution (1.092 M). [C$_1$ted] [MOPS] was prepared by sequential addition of MOPS (1.9252 g, 9.2 mmol) to [C$_1$ted] [OH] (0.92 M, 10 mL, 9.2 mmol) to a 5.6492 g plastic centrifuge tube and used as an aqueous solution. [C$_1$ted] [tau] was prepared by sequential addition of Taurine (1.1516 g, 9.2 mmol) to [C$_1$ted] [OH] (0.92 M, 10 mL, 9.2 mmol) to a 5.5837 g plastic centrifuge tube and used as an aqueous solution.

A ternary, equi-molar mixture of the three IL was prepared by the addition of [C$_1$ted] [MOPS] (0.92 M, 3.265 mL, 3 mmol), [C$_1$ted] [tau] (0.92 M, 3.265 mL, 3 mmol), and [C$_1$ted] [ise] (1.092M, 2.75 mL, 3 mmol) to 5.4292 g plastic centrifuge tube. The ternary mixture of aqueous solutions was mixed by shaking the closed vial. Solutions with [C$_1$ted] [OH] were prepared by mixing of aqueous solutions of the ternary mixture and [C$_1$ted] [OH] (3.5 M, saturated with zinc oxide) in a manner such that [OH] comprised between 20 and 80 mol % of the anions present in the mixture, thus forming the quaternary mixture. Water was removed from samples of quaternary mixtures by rotary evaporation. The solutions retained water between 0 and 9 wt % and were liquid at ambient conditions.

The samples were exposed to a controlled atmosphere which contained 5% relative humidity for three days and showed no signs of solidification, whereas the pure [C$_1$ted] [OH] control sample solidified. Subsequent testing showed that the mixtures remained liquid when exposed to 5% relative humidity for a period of time in excess of 31 days in the presence of nucleation sites (in the form of a zinc wire and powdered zinc oxide) added to the samples to promote solidification. Electrochemical testing showed that the quaternary mixture was chemically and electrochemically stable in a potential range of 3V on both zinc and platinum working electrodes.

Example 11

[C$_1$impd][ise]

[C$_1$impd][ise] is an IL comprised of 1-methylimidazo[1,2-a]pyridinium (C$_1$impd) as the cation and isethionate (ise) as the anion. [C$_1$impd]$_2$[SO$_4$] (3.166 g, 8.74 mmol) was prepared from imidazo[1,2-a]pyridine and dimethylsulfate in accordance with the following dialkyl sulfate synthesis reaction:

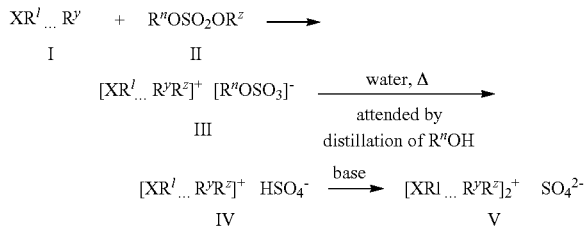

where XR$^1$ . . . R$^y$ is imidazo[1,2-a]pyridine (impd), and R"OSO$_2$OR$^z$ is dimethyl sulfate. Reaction Product III is:

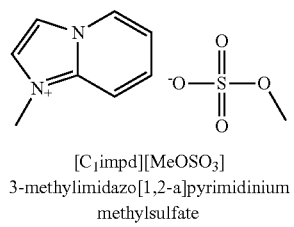

[C$_1$impd][MeOSO$_3$]
3-methylimidazo[1,2-a]pyrimidinium
methylsulfate

Reaction product IV is:

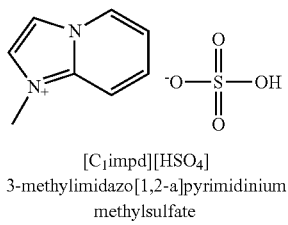

[C₁impd][HSO₄]
3-methylimidazo[1,2-a]pyrimidinium
methylsulfate

Reaction product V is:

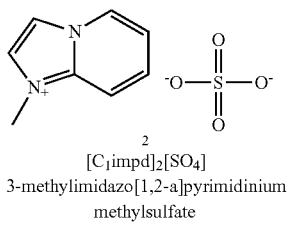

[C₁impd]₂[SO₄]
3-methylimidazo[1,2-a]pyrimidinium
methylsulfate

Reaction product V, [C₁impd]₂[SO₄] (3.166 g, 8.74 mmol) was dissolved in 2:1 alcohol-water (30 mL), whereupon a prepared solution of sodium isethionate (2.592 g, 17.50 mmol) in 2:1 alcohol-water (18 mL) was added to it with stirring. The resulting slurry was stirred for about 2 h, whereupon it was suction filtered, and the filtrate was concentrated as far as feasible by rotary evaporation. The residue was taken up in methanol (25 mL) and loaded onto an about 12-g column of 230-400 mesh silica gel previously packed in methanol.

As in Example 3, the methanolic solution of crude [C₁impd][ise] was pushed down to the level of the top of the silica gel bed with air pressure while the column issue was collected in a 250-mL round bottom flask; the flask previously containing the crude product was rinsed with methanol (25 mL) and the rinse methanol was similarly loaded and pressed down while the column issue was collected on top of the first fraction. The rinsing process was repeated once before the silica gel column was washed down with fresh methanol (125 mL), all the while collecting the column issue on top of the accumulated methanol solution. The combined methanolic fractions were concentrated by rotary evaporation to produce purified [C₁impd][ise] (4.122 g, 15.96 mmol, 91%) as an ionic liquid. The ionic liquid of Example 11 slowly solidified at ambient conditions. Specifically, it was freely liquid when contained in a flask immersed in an 80° C. water bath; it remained liquid for several hours after it was removed from the water bath. Thereafter, several regions of the liquid began to slowly solidify independently of each other, and after about 1 day, the IL had turned thoroughly solid under ambient conditions.

The embodiments and examples have been provided solely to illustrate embodiments of the invention and should not be considered limiting. To the contrary, the embodiments encompass all modifications, substitutions, alterations, and equivalents with in the spirit and scope described herein.

What is claimed is:

1. A room temperature ionic liquid having a melting point at or below 100° C. at 1 atmosphere comprising an isethionate ion and a cation selected from the group consisting of 1-methyl-1,4-diazabicyclo[2.2.2]octanium, 1-ethyl-2,3-dimethylimidazolium, N-ethyl-N-methylmorpholinium, 1-methylimimdazo[1,2-a]pyridinium, tetramethylammonium, and mixtures thereof.

2. The room temperature ionic liquid of claim 1, wherein the cation is 1-methyl-1,4-diazabicyclo[2.2.2]octanium.

3. The room temperature ionic liquid of claim 1, wherein the cation is tetramethylammonium.

4. The room temperature ionic liquid of claim 1, wherein the cation is 1-ethyl-2,3-dimethylimidazolium.

5. A metal-air cell comprising a fuel electrode for oxidizing a fuel, an air electrode configured to absorb and reduce gaseous oxygen, and a room temperature ionic liquid comprising a sulfonate ion selected from the group consisting of isethionate ([ise]), taurinate ([tau]), 3-morpholinopropanesulfonate (MOPS), 4-(2-hydroxyethyl)-1-piperazinepropanesulfonate (HEPPS, EPPS), 1,4-piperazinediethanesulfonate (PIPES), N-(2-acetamido)-2-aminoethanesulfonate (ACES), N-cyclohexyl-3-aminopropanesulfonate (CAPS), 4-(2-hydroxyethyl)-1-piperazineethanesulfonate (HEPES), 2-[(2-hydroxy-1,1-bis(hydroxymethyl)ethyl)amino]ethanesulfonate (TES), N-[tris(hydroxymethyl)methyl]-3-aminopropanesulfonate (TAPS), 3-(N-tris[hydroxymethyl]methylamino)-2-hydroxypropanesulfonate (TAPSO), and mixtures thereof, and a cation selected from the group consisting of 1-methyl-1,4-diazabicyclo[2.2.2]octanium, 1-ethyl-2,3-dimethylimidazolium, N-ethyl-N-methylmorpholinium, 1-methylimimdazo[1,2-a]pyridinium, tetramethylammonium, and mixtures thereof.

6. The metal-air cell of claim 5, wherein the sulfonate ion is isethionate.

7. The metal-air cell of claim 5, wherein the sulfonate ion is taurinate.

8. The metal-air cell of claim 5, wherein the cation is 1-methyl-1,4-diazabicyclo [2.2.2]octanium.

9. The metal-air cell of claim 5, wherein the cation is tetramethylammonium.

10. The metal-air cell of claim 5, wherein the cation is 1-ethyl-2,3-dimethylimidazolium.

11. An ionically conductive medium for use in an electrochemical cell comprising a room temperature ionic liquid having a melting point at or below 100° C. at 1 atmosphere comprising an isethionate ion and a cation selected from the group consisting of 1-methyl-1,4-diazabicyclo[2.2.2]octanium, 1-ethyl-2,3-dimethylimidazolium, N-ethyl-N-methylmorpholinium, 1-methylimimdazo[1,2-a]pyridinium, tetramethylammonium, and mixtures thereof.

12. The ionically conductive medium of claim 11, wherein the cation is 1-methyl-1,4-diazabicyclo[2.2.2]octanium.

* * * * *